United States Patent [19]

Hefner, Jr.

[11] Patent Number: 4,558,115
[45] Date of Patent: Dec. 10, 1985

[54] THERMOSETTABLE RESIN COMPOSITIONS CONTAINING A POLYEPOXIDE AND AN ALKENYL PHENYL CYANATE

[75] Inventor: Robert E. Hefner, Jr., Lake Jackson, Tex.

[73] Assignee: The Dow Chemical Company, Midland, Mich.

[21] Appl. No.: 710,356

[22] Filed: Mar. 11, 1985

Related U.S. Application Data

[63] Continuation-in-part of Ser. No. 639,034, Aug. 9, 1984, abandoned.

[51] Int. Cl.[4] ...................... C08G 59/40; C08G 59/46; C08G 73/08
[52] U.S. Cl. ...................................... 528/92; 525/502; 528/97; 528/98; 528/117; 528/119; 528/322; 528/393; 523/466
[58] Field of Search .................... 525/502; 528/92, 97, 528/98, 117, 119, 322, 393; 523/466

[56] References Cited

U.S. PATENT DOCUMENTS

| | | | |
|---|---|---|---|
| 4,110,364 | 8/1978 | Gaku et al. | 528/117 X |
| 4,116,946 | 9/1978 | Jakob et al. | 528/392 X |
| 4,298,720 | 11/1981 | Yamazaki et al. | 526/262 |
| 4,369,302 | 1/1983 | Ikeguchi et al. | 528/117 X |
| 4,369,304 | 1/1983 | Gaku et al. | 528/117 X |
| 4,370,467 | 1/1983 | Gaku et al. | 528/117 X |
| 4,371,689 | 2/1983 | Gaku et al. | 528/392 X |
| 4,383,903 | 5/1983 | Ayano et al. | 528/117 X |
| 4,393,195 | 7/1983 | Gaku et al. | 528/117 X |
| 4,401,777 | 8/1983 | Tsuboi et al. | 528/117 X |

*Primary Examiner*—Earl Nielsen
*Attorney, Agent, or Firm*—James G. Carter

[57] ABSTRACT

Compositions comprising a material containing (a) alkenyl phenyl cyanate groups, (b) a material containing epoxide groups and optionally any one or more of (c) an aromatic polycyanate, (d) a polymaleimide or (e) a polymerizable ethylenically unsaturated aromatic material are curable to products having excellent mechanical, thermal and chemical resistant properties.

42 Claims, No Drawings

THERMOSETTABLE RESIN COMPOSITIONS CONTAINING A POLYEPOXIDE AND AN ALKENYL PHENYL CYANATE

CROSS REFERENCE TO RELATED APPLICATION

This is a continuation-in-part of my copending application Ser. No. 639,034 filed Aug. 9, 1984, and now abandoned.

BACKGROUND OF THE INVENTION

This invention relates to thermosettable resin compositions having excellent physical and mechanical properties.

Resins containing the epoxide group and resins containing the cyanate group are both known thermosettable materials. However, there is much room for improvement in the mechanical properties and moisture resistance of said thermoset resins. Bismaleimide resins are known for their excellent heat resistance, however, they are difficult to process and cure due to high melting points, poor solvent solubility and slow curing rates. The resulting cured bismaleimides are highly cross-linked and thus provide brittle polymeric products.

The present invention provides novel compositions which are thermosettable to useful polymeric (cured) compositions with excellent mechanical strength, improved processability, high reactivity, low moisture sensitivity and excellent heat resistance. These compositions are useful in the preparation of castings, laminates, coatings and the like.

SUMMARY OF THE INVENTION

One aspect of the present invention pertains to a composition which comprises
(A) from about 1 to about 99, preferably from about 1 to about 75, most preferably from about 5 to about 50 percent by weight of at least one alkenyl phenyl cyanate;
(B) from about 1 to about 99, preferably from about 1 to about 75, most preferably from about 5 to about 50 percent by weight of at least one material having an average of more than one vicinal epoxide group per molecule;
(C) from zero to about 98, preferably from about 5 to about 90, most preferably from about 25 to about 80 percent by weight of at least one aromatic polycyanate;
(D) from zero to about 50, preferably from zero to about 20, most preferably from zero to about 5 percent by weight of at least one polymaleimide; and
(E) from zero to about 98, preferably from zero to about 50, most preferably from zero to about 20 percent by weight of at least one polymerizable ethylenically unsaturated aromatic monomer.

Another aspect of the present invention pertains to the products resulting from curing the aforementioned composition.

DETAILED DESCRIPTION OF THE INVENTION

Suitable alkenyl phenyl cyanates which can be employed herein include, for example, those represented by the formula

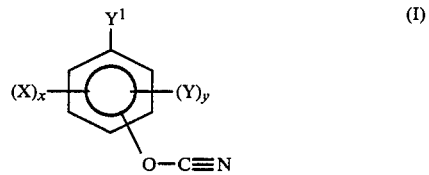

wherein each R, $R^1$ and $R^2$ is independently hydrogen or a hydrocarbyl group having from 1 to about 3 carbon atoms; each X is independently hydrogen, a hydrocarbyl or hydrocarbyloxy group having from 1 to about 6 carbon atoms, chlorine or bromine; each Y is independently hydrogen or a hydrocarbyl group having from 1 to about 4 carbon atoms; $Y^1$ is a

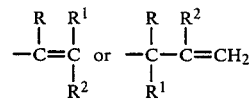

group; and x and y are positive integers and the sum of x plus y is 4.

The term hydrocarbyl as employed herein means any aliphatic, cycloaliphatic, aromatic, aryl substituted aliphatic or aliphatic substituted aromatic groups. Likewise, the term hydrocarbyloxy group means hydrocarbyl group having an oxygen linkage between it and the object to which it is attached.

Particularly suitable alkenyl phenyl cyanates represented by formula I include, for example, p-isopropenylphenyl cyanate, p-vinylphenyl cyanate, m-vinylphenyl cyanate, methyl-p-isopropenylphenyl cyanate, 3-chloro-4-isopropenylphenyl cyanate, p-allylphenyl cyanate, p-methallylphenyl cyanate, m-allylphenyl cyanage, 2,6-dimethyl-4-allylphenyl cyanate, mixtures thereof and the like. It is most preferred that the alkenyl phenyl cyanate be substantially free of dimeric and/or oligomeric components although it is operable to use an alkenyl phenyl cyanate containing substantial (up to 90 percent by weight) dimeric and/or oligomeric components. Said components are formed during the cyanation reaction of an alkenylphenol containing the corresponding dimeric diphenols and/or oligomeric polyphenols.

The alkenyl phenyl cyanates are conveniently prepared by reacting a stoichiometric quantity or a slight stoichiometric excess (up to about 20 percent excess) of a cyanogen halide with an alkenyl phenol in the presence of a stoichiometric quantity of a base material.

Suitable alkenyl phenols include, for example, those represented by the formula

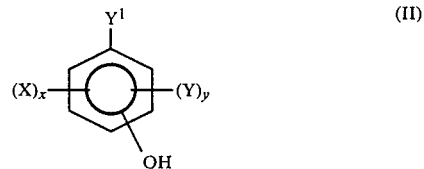

wherein R, $R^1$, $R^2$, X, Y, $Y^1$, x and y are as hereinbefore defined.

Suitable cyanogen halides include cyanogen bromide and cyanogen chloride. Alternately, the method of Martin and Bauer described in Organic Synthesis, Volume 61, pp. 35-68 (1983) and published by John Wiley and Sons can be used to generate the required cyanogen halide in situ from sodium cyanide and a halogen such as chlorine or bromine.

Suitable bases include both inorganic bases and tertiary amines such as sodium hydroxide, potassium hydroxide, triethylamine, mixtures thereof and the like. Most preferred as the base is triethylamine.

Suitable solvents include water, acetone, chlorinated hydrocarbons, ketones and the like. Most preferred solvents are acetone and methylene chloride. Reaction temperatures of from about −40° to about 60° C. are operable with temperatures of −20° to 25° C. being preferred.

Suitable materials having an average of more than one vicinal epoxy group per molecule include, for example, the glycidyl ethers represented by the formulas

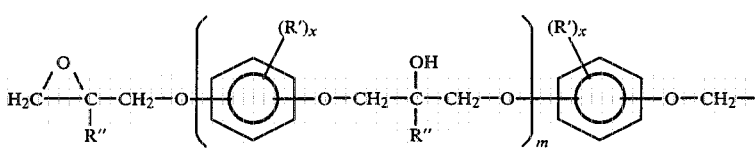

III.

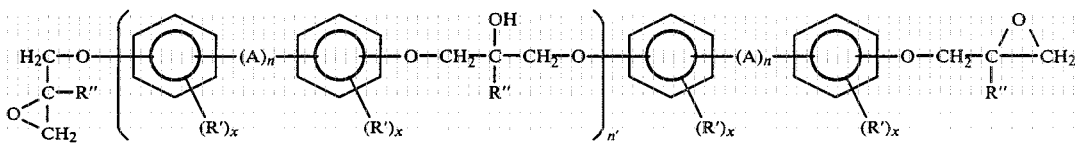

IV.

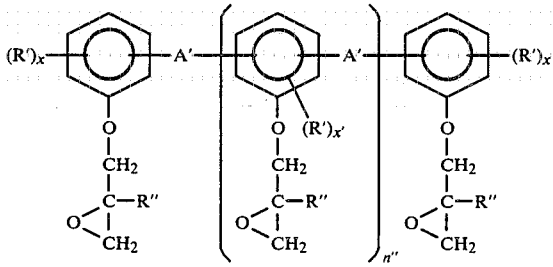

V.

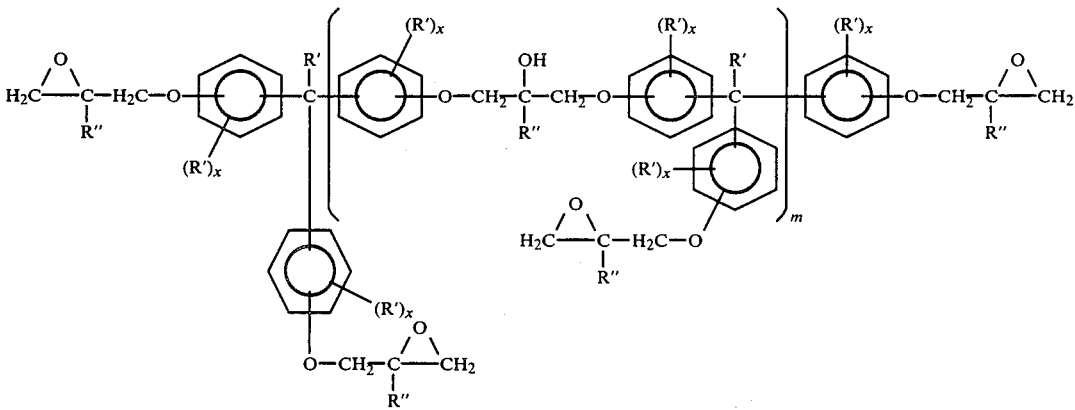

VI.

wherein each A is independently a divalent hydrocarbon group having from 1 to about 10 carbon atoms, preferably from 1 to about 4 carbon atoms,

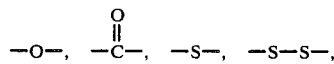

each A′ is independently a divalent hydrocarbon group having from 1 to about 6, preferably from 1 to about 4 carbon atoms or a

group; p has a value of from zero to about 10, preferably from zero to 3; each R′ is independently hydrogen, a hydrocarbyl or hydrocarbyloxy group having from 1 to about 10, preferably from 1 to about 4 carbon atoms, halogen, preferably chlorine or bromine; each R″ is independently hydrogen or an alkyl group having from 1 to about 4 carbon atoms; n has a value of zero or 1; n' has a value of from about zero to about 30, preferably from about zero to about 5; n" has a value of from about 0.001 to about 6, preferably from about 0.01 to about 3; x has a value of 4 and x' has a value of 3.

Particularly suitable polyepoxides which can be employed herein include, for example, the diglycidyl ethers of resorcinol, bisphenol A, 3,3',5,5'-tetrabromobisphenol A, the triglycidyl ether of tris(hydroxyphenyl) methane, the polyglycidyl ether of a phenol-formaldehyde condensation product (novolac), the polyglycidyl ether of a dicyclopentadiene and phenol condensation product and the like. The polyepoxides can be used either alone or in combination.

The aforementined polyepoxides represented by formulas III, IV, V and VI can be prepared by reaction of a diphenol or polyphenol with an epihalohydrin and a basic acting material. Said reaction generally involves two distinct steps: coupling reaction of the epihalohydrin and diphenol or polyphenol to provide a halohydrin intermediate and dehydrohalogenation reaction of the halohydrin intermediate to provide the glycidyl ether product. Suitable catalysts and reaction conditions for preparing polyepoxides are described in the *Handbook of Epoxy Resins* by Lee and Neville, McGraw-Hill (1967) which is incorporated herein by reference.

Suitable aromatic polycyanates which can be employed herein include, for example, those represented by the formulas

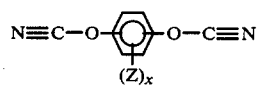 (VII)

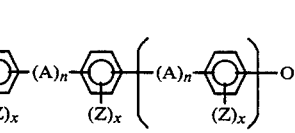 (VIII)

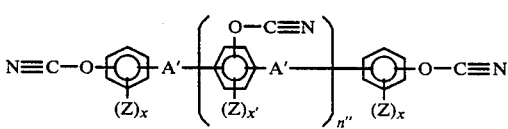 (IX)

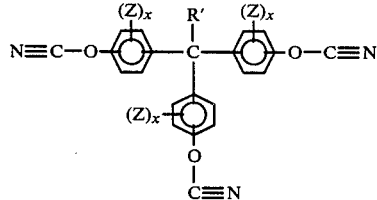 (X)

wherein each Z is independently hydrogen, a hydrocarbyl or hydrocarbyloxy group having from 1 to about 4 carbon atoms, chlorine, bromine, or a —O—C≡N group; m has a value of zero to about 100, preferably from zero to about 10 and A, A', R', x, x', n, n" and p are as hereinbefore defined.

Suitable aromatic polycyanates represented by formulas VII, VIII, IX and X include, for example, bisphenol A dicyanate, the dicyanates of 4,4'-dihydroxydiphenyl oxide, resorcinol, 4,4'-thiodiphenol, 4,4'-sulfonyldiphenol, 3,3',5,5'-tetrabromobisphenol A, 2,2',6,6'-tetrabromobisphenol A, 3-phenyl bisphenol A, 4,4'-dihydroxybiphenyl, 2,2'-dihydroxybiphenyl, 2,2',4,4'-tetrahydroxydiphenyl methane, 2,2',6,6'-tetramethyl-3,3',5,5'-tetrabromobisphenol A, 5,5'-dimethoxybisphenol A, the tetracyanate of 2,2',4,4'-tetrahydroxydiphenylmethane,

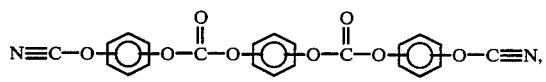

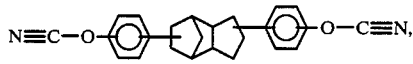

the tricyanate of tris(hydroxyphenyl)methane, the polycyanate of a phenolformaldehyde condensation product (novolac), the polycyanate of a dicyclopentadiene and phenol cndensation product, and the like. The aromatic polycyanates may be used either alone or in any combination.

The aromatic polycyanates can be prepared by reacting a stoichiometric quantity or slight stoichiometric excess (up to about 20 percent excess) of a cyanogen halide with an aromatic polyphenol in the presence of a stoichiometric quantity of a base.

Suitable aromatic polyphenols include, for example, those represented by the formulas

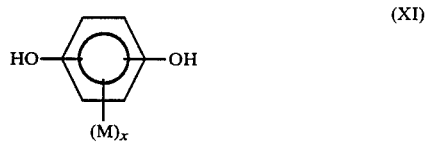 (XI)

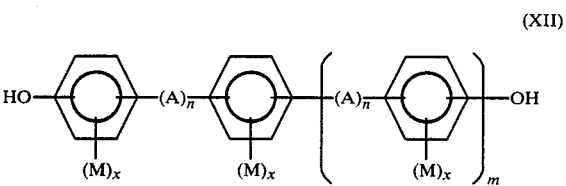 (XII)

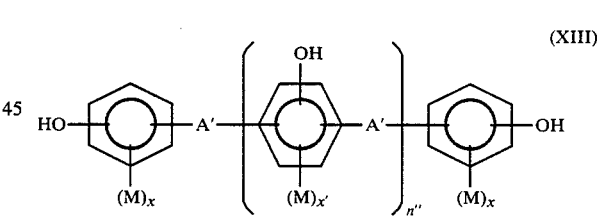 (XIII)

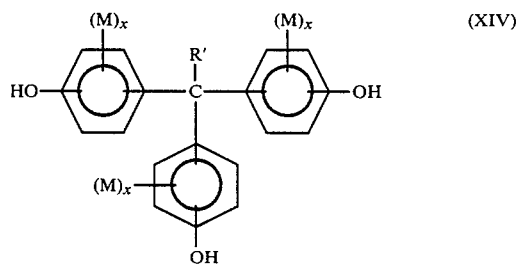 (XIV)

wherein A, A', R', x, x', n, n", m and p are as hereinbefore defined, and each M is independently a hydrocarbyl or hydrocarbyloxy group having from 1 to about 4 carbon atoms, chlorine, bromine, a phenyl group or a hydroxyl group.

Suitable cyanogen halides include cyanogen bromide and cyanogen chloride. Alternately, the method of Martin and Bauer described in Organic Synthesis, Volume 61, pp. 35–68 (1983) and published by John Wiley and Sons can be used to generate the required cyanogen halide in situ from sodium cyanide and a halogen such as chlorine or bromide.

Suitable bases include both inorganic bases and tertiary amines such as sodium hydroxide, potassium hydroxide, triethylamine, mixtures thereof and the like. Most preferred as the base is triethylamine.

Suitable solvents include water, acetone, chlorinated hydrocarbons, ketones, and the like. Most preferred solvents are acetone and methylene chloride.

Reaction temperatures of from about −40° to about 60° C. are operable with temperatures of −20° to 25° C. being preferred.

Suitable polymaleimides which can be employed herein include, for example, those represented by the formulas

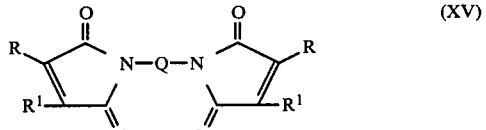
(XV)

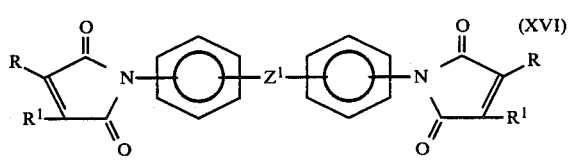
(XVI)

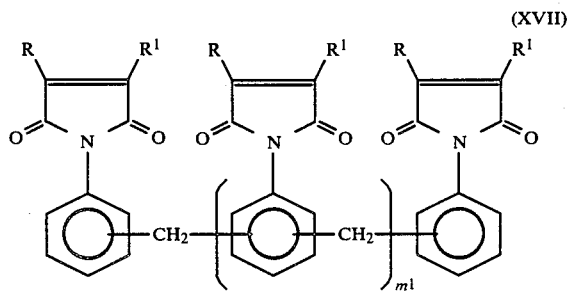
(XVII)

wherein R and R' are as hereinbefore defined; $Z^1$ is a direct bond, a divalent hydrocarbyl group having from 1 to about 5 carbon atoms —S—, —S—, —O—,

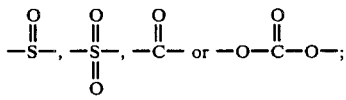

Q is a divalent hydrocarbyl group having from 2 to about 12 carbon atoms and $m^1$ has a value of 0.001 to about 10.

Typical polymaleimides represented by formulas XV, XVI and XVII include, N,N'-ethylenebismaleimide, N,N'-ethylenebis(2-methylmaleimide), N,N'-hexamethylenebismaleimide, N,N'-(oxydi-p-phenylene)bismaleimide, N,N'-(methylenedi-p-phenylene)bismaleimide, N,N'-(methylenedi-p-phenylene)bis(2-methylmaleimide), N,N'-(thiodi-p-phenylene)bismaleimide, N,N'-(sulfonyldi-m-phenylene)bismaleimide, N,N'-(isopropylidenedi-p-phenylene)bismaleimide, polymethylene polyphenylene polymaleimides and the like. The polymaleimides may be used either alone or in any combination.

The polymaleimides can be prepared by reacting a stoichiometric quantity of a maleic anhydride per amine group of a polyamine in the presence of a suitable solvent.

Suitable maleic anhydrides include, for example, those represented by the formula

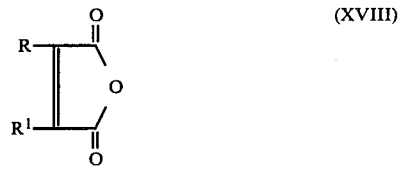
(XVIII)

wherein R and $R^1$ are as hereinbefore defined.

Suitable maleic anhydrides include maleic anhydride, methyl maleic anhydride, mixtures thereof and the like. Most preferred as the maleic anhydride is maleic anhydride, per se.

Suitable polyamines which can be employed to prepare the polymaleimides include, for example, those represented by the formulas

(XIX)

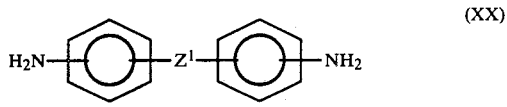
(XX)

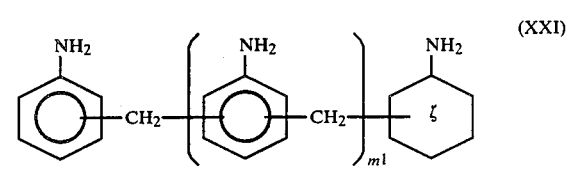
(XXI)

wherein Q, $Z^1$ and $m^1$ are as hereinbefore defined.

Suitable polyamines include 1,4-diaminobutane, dodecyl diamine, methylene dianiline, diaminodiphenyl ether, 2-methyl-4-ethyl-1,8-diaminooctane, anilineformaldehyde condensation products, mixtures thereof and the like.

Suitable solvents include aromatic hydrocarbons, chlorinated hydrocarbons, N,N-dimethylformamide and the like. Most preferred solvents are N,N-dimethylformamide, chloroform and toluene. The polymaleamic acid resulting from reaction of a maleic anhydride and a polyamine may be isolated then dehydrated to the desired polymaleimide. Alternately, the reaction may be performed in a single continuous step. Detailed procedures for preparing polymaleimides can be found in U.S. Pat. Nos. 2,444,536 and 2,462,835.

Suitable polymerizable ethylenically unsaturated aromatic materials which can be employed herein include those represented by the formula

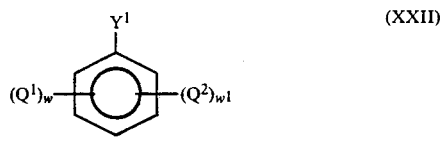
(XXII)

wherein R, $R^1$, $R^2$ and $Y^1$ are as previously defined, each $Q^1$ is independently hydrogen, a hydrocarbyl or hydrocarbyloxy group having from 1 to about 4 carbon atoms, a vinyl group, an allyl group, chlorine or bromine; each $Q^2$ is independently hydrogen or a hydrocarbyl or hydrocarbyloxy group having from 1 to about 4 carbon atoms and w and $w^1$ are each positive integers, the sum of which is 5.

Typically ethylenically unsaturated compounds represented by formula XXII include, for example, styrene, alpha-methylstyrene, chlorostyrene, bromostyrene, t-butylstyrene, p-methylstyrene, p-methoxystyrene, divinylbenzene, propylstyrene, chloro-lpha-methylstyrene, m-methylstyrene, o-methylstyrene, allylbenzene, methallylbenzene, p-allylstyrene, diallylbenzene, mixtures thereof and the like.

Compositions which comprise an alkenyl phenyl cyanate (I), a polyepoxide (III, IV, V, VI), optionally an aromatic polycyanate (VII, VIII, IX, X), optionally a polymaleimide (XV, XVI, XVII) and optionally an ethylenically unsaturated compound (XXII) may be cured (polymerized) by heating from 50° to about 350° C. or more, preferably by heating from 70° to 200° C. and optionally in the presence of 0.001 to 5 percent of a suitable cyclization catalyst and, optionally, 0.001 to 2 percent of a suitable free radical forming catalyst. Operable cyclization catalysts include those taught by U.S. Pat. Nos. 3,694,410 and 4,094,852.

Most preferred cyclization catalysts are cobalt naphthenate and cobalt octoate. The quantity depends upon the particular cyclization catalyst, cure temperature, and polymerizable monomers employed but usually from about 0.001 to about 5 percent by weight is adequate. Operable free radical forming catalysts include the organic peroxides and azo or diazo compounds. Most preferred free radical forming catalysts are t-butyl peroxybenzoate, azobisisobutyronitrile, dicumylperoxide and di-t-butyl peroxide. The quantity depends upon the particular free radical forming catalyst, cure temperature and the particular monomers employed but usually from about 0.001 to about 2 percent by weight is suitable.

Prepolymerization or B-staging of the compositions can be accomplished by using lower temperatures and/or shorter curing times. Curing of the thus formed prepolymerized or B-staged resin can then be completed at a later time or immediately following prepolymerization or B-staging by increasing the temperature and/or curing time.

The cured (copolymerized) products possess a complex variety of curing structures which depend, in part, upon the amounts and types of alkenylphenyl cyanate (I), polyepoxide (III, IV, V, VI), optionally an aromatic polycyanate (VII, VIII, IX, X), optionally a polymaleimide (XV, XVI, XVII) and optionally an ethylenically unsaturated aromatic compound (XXII).

Compositions which contain the cyanate group, —O—C≡N, (formulas I, VII, VIII, IX, X) and the glycidyl ether group,

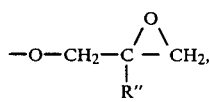

(formulas III, IV, V, VI) copolymerize to produce several curing structures one of which is tentatively designated as an oxazoline. This curing structure may be made up of several actual chemical structures including one or more derived from ring opening reaction products. A further curing structure is the triazine group,

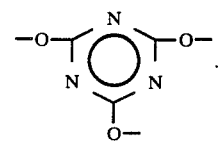

The relative amounts of the aforementioned structures within the polymer can be controlled by varying the mole ratio of —C≡N groups of the cyanate to the

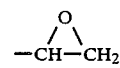

groups of the glycidyl ether. A one to one mole ratio of —C≡N to

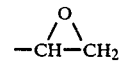

groups (stoichiometric) principly produces the oxazoline curing structures in the copolymer. A greater than stoichiometric ratio of —C≡N to

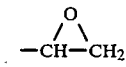

groups (greater —C≡N stoichiometry) produces a mixture of oxazoline and triazine curing structures.

Compositions which contain polymerizable ethylenically unsaturated groups (formulas I, XV, XVI, XVII and XXII) homo and copolymerize to produce crosslinked curing structures. Homo and copolymerization is also meant to include both dimerization and oligomerization.

A specific example is the curing structure derived from vinyl copolymerization of p-isopropenylphenyl cyanate (formula I where X is —H, Y is —H, x+y is 4, R is —CH₃, $R^1$ is —H, $R^2$ is —H) and the bismaleimide of methylenedianiline (formula XVI where R is —H, $R^1$ is —H, $Z^1$ is —CH₂—):

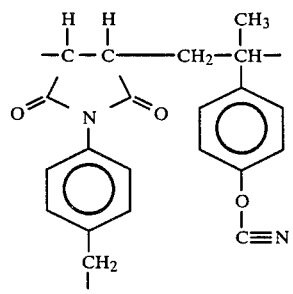

Compositions which contain polymerizable ethylenically unsaturated groups (formulas I, XV, XVI, XVII, XXII) and compositions which contain the cyanate group (formulas I, VII, VIII, IX, X) copolymerize to produce curing structures. Numerous combinations of these curing structures are possible. For example, copolymerization of p-isopropenylphenyl cyanate (formula I where X is —H, Y is —H, x+y is 4, R is —CH$_3$, R$^1$ is —H, R$^2$ is —H), the bismaleimide of methylenedianiline (formula XVI where R is —H, R$^1$ is —H, Z$^1$ is —CH$_2$—) and bisphenol A dicyanate (formula VIII where Z is —H, A is

x is 4, n is 1, m is 0) provides the following as one of the curing structure possibilities:

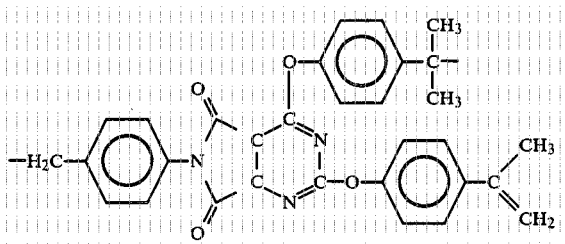

As a second example, copolymerization of p-isopropenylphenyl cyanate (formula I where X is —H, Y is —H, x+y is 4, R is —CH$_3$, R$^1$ is —H, R$^2$ is —H), bisphenol A dicyanate (formula VIII where Z is —H, A is

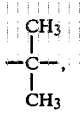

x is 4, n is 1, m is 0) and styrene (formula XXII where Y$^1$ is

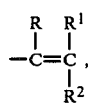

R is —H, R$^1$ is —H, R$^2$ is —H, Q$^1$ is —H, Q$^2$ is —H, w+w$^1$ is 5) provides the following as one of the curing structure possibilities:

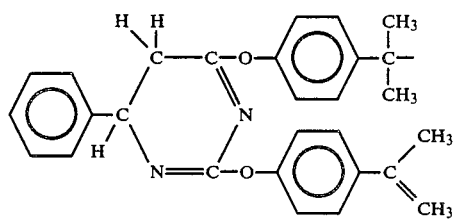

The amounts and types of curing structures present in the copolymerized (cured) products of the present invention can additionally be influenced by the presnce or absence of a cyclization catalyst as well as its specific composition, the presence or absence of a free-radical forming catalyst as well as its specific composition, the cure time, the cure temperature and other variables.

Compositions which comprise an alkenyl phenyl cyanate (I), a polyepoxide (III, IV, V, VI), optionally an aromatic polycyanate (VII, VIII, IX, X), optionally a polymaleimide (XV, XVI, XVII) and optionally an ethylenically unsaturated compound (XXII) may be cured (polymerized) either simultaneously or in stages. As a specific example, copolymerization of two moles of p-isopropenylphenyl cyanate and one mole of the diglycidyl ether of bisphenol A in the presence of a suitable cyclization catalyst can be performed under reaction conditions which lead to a degree of conversion which does not preclude dissolution in styrene. Said composition is then dissolved in styrene and copolymerized therewith. Alternately, p-isopropenylphenyl cyanate, the diglycidyl ether of bisphenol A and styrene are combined then simultaneously copolymerized.

In those instances where X is chlorine or bromine (formula I), R' is chlorine or bromine (formulas III, IV, V, VI), Z is chlorine or bromine (formulas VII, VIII, IX, X) and/or Q$^1$ is chlorine or bromine (formula XXII) the halogen(s) are incorporated into the copolymers by the polymerization of monomer(s) containing said group(s). Furthermore, the halogen groups can be incorporated into the copolymers in a specific location within the polymer structure. As a specific example, copolymerization of p-isopropenylphenyl cyanate, the diglycidyl ether of bisphenol A and chlorostyrene provide a copolymer wherein Q$^1$ is chlorine and Q$^1$ is specifically present only on the styrene aromatic rings within the polymer chains. Said products, where X is chlorine or bromine (formula I), R$^{40}$ is chlorine or bromine (formulas III, IV, V, VI), Z is chlorine or bromine (formulas VII, VIII, IX, X) and/or Q$^1$ is chlorine or bromine (formula XXII), are useful as fire retardant polymers.

If desired, the compositions can contain fillers, pigments, dyes, reinforcing materials, other additives and the like.

The compositions of the present invention are useful in the reparation of castings, structural or electrical laminates or composites, coatings, and the like.

Laminates or composites can be prepared from the compositions of the present invention employing any facing and/or reinforcing materials such as, for example, metallic sheets, woven or mat materials, such as fiberglass, graphite, asbestos, aramids, carbon combinations thereof and the like.

The following examples are illustrative of the invention but are not to be construed as to limiting the scope thereof in any manner.

EXAMPLE 1

A. Preparation of p-Isopropenylphenyl Cyanate

A 134.17 gram portion of p-isopropenylphenol (1.00 mole), 111.23 grams of cyanogen bromide (1.05 mole) and 600 milliliters of acetone were added to a reactor and maintained under a nitrogen atmosphere with stirring. The p-isopropenylphenol used herein was of in excess of 99 percent purity. The stirred solution was cooled to −10° C. then 101.19 grams of triethylamine (1.00 mole) was added to the reactor over a twenty minute (1200 s) period and so as to maintain a reaction temperature of −5° to −2° C. After completion of the triethylamine addition, the reactor was maintained at −2° to 5° C. for an additional thirty minutes (1800 s), followed by addition of the reactor contents to 1 gallon of chilled deionized water. After five minutes (300 s) the water and product mixture was multiply extracted with three 400 milliliter volumes of methylene chloride. The combined methylene chloride extract was washed with 500 milliliters of 5 percent aqueous hydrochloric acid followed by washing with 800 milliliters of deionized water then drying over anhydrous sodium sulfate. The dry methylene chloride extract was filtered and solvent removed by rotary evaporation under vacuum. p-Isopropenylphenyl cyanate (132.5 grams) was recovered in 83.2 percent yield as a transparent light amber colored liquid. Infrared spectrophotometric analysis of a film sample of the product confirmed the product structure (disappearance of phenolic hydroxyl group, appearance of —C≡N group). Gas chromatographic-mass spectroscopic analysis of the product confirmed the structure for p-isopropenylphenyl cyanate (parent ion m/e=159) with essentially no other compounds being present.

B. Preparation of Bisphenol A Dicyanate

A 228.3 gram portion of 4,4'-isopropylidenediphenol (1.50 moles), 333.68 grams of cyanogen bromide (3.15 moles) and 1000 milliliters of acetone were added to a reactor and maintained under a nitrogen atmosphere with stirring. The stirred solution was cooled to −5° C. then 305.09 grams of triethylamine (3.015 moles) was added to the reactor over a twenty-four minute (1440 s) period and so as to maintain the reaction temperature at −5° to 0° C. After completion of the triethylamine addition, the reactor was maintained at 0° to 7° C. for an additional forty-five minutes (2700 s), followed by addition of the reactor contents to 1 gallon of chilled deionized water. After twenty minutes (1200 s) the water and product mixture was extracted with three 500 milliliter portions of methylene chloride. The combined methylene chloride extract was washed with 500 milliliters of 5 percent aqueous hydrochloric acid followed by washing with 1000 milliliters of deionized water then drying over anhydrous sodium sulfate. The dry methylene chloride solution was filtered and solvent removed by rotary evaporation under vacuum. Bisphenol A dicyanate (393.8 grams) was recovered in 94.3 percent yield as a white crystalline solid. Infrared spectrophotometric analysis of a film sample of the product confirmed the product structure (disappearance of phenolic hydroxy group, appearance of —C≡N group).

C. Preparation and B-Staging of a Bisphenol A Dicyanate, p-Isopropenylphenyl Cyanate and Epoxide Resin Solution A 4.12 gram portion of p-isopropenylphenyl cyanate from A above, 21.78 grams of bisphenol A dicyanate from B above, 33.4 grams of a diglycidyl ether of bisphenol A having an epoxide equivalent weight (EEW) of 183, and 0.025 gram of cobalt naphthenate (6.0 percent active) were combined to form a mixture. This mixture was heated to 100° C. for 10 minutes (600 s) to provide a B-staged product which was recovered as a transparent, light green colored solution at room temperature (25° C.).

D. Use of B-Staged Bisphenol A Dicyanate, p-Isopropenylphenyl Cyanate and Epoxide Resin Solution in Preparation of a Cured Glass Laminate The 59.3 grams of the B-staged bisphenol A dicyanate, p-isopropenylphenyl cyanate, and diglycidyl ether of bisphenol A solution from C above and 150 grams of methylene chloride were combined to form a solution. This solution was filtered and then 0.125 gram of cobalt naphthenate (6.0 percent active) was added. A set of three 12-inch by 12-inch (304.8 mm by 304.8 mm) woven fiberglass cloth pieces were then equally impregnated with the solution. The fiberglass cloth used was a commercial-grade product treated with a proprietary coupling agent (Burlington 76–28 electrical laminating cloth) and had an average weight of 0.14 gram per square inch (0.0217 g/cm²). The set of impregnated cloths were allowed to dry for one hour (3600 s) at room temperature (25° C.) followed by additional drying in a vented forced-air, convection-type oven for nine minutes (540 s) at 70° C., 20 minutes (1200 s) at 100° C., then for five minutes (300 s) at 125° C. Each cloth was cooled and found to be tack-free at room temperature and then cut to provide ten 6-inch by 6-inch (152.4 mm by 152.4 mm) pieces which were loaded into a stainless steel frame and placed between stainless steel plates which had been treated with a silicone mold release. The plates were loaded into a 177° C. hot press (Pasadena Hydraulics, Inc., Model P-215) and maintained for two hours (7200 s) at 5000 psi (34.5 MPa). After this time a 6-inch by 6-inch by 1/16-inch (152.4 mm by 152.4 mm by 1.5785 mm) semi-transparent, pale green colored, rigid laminate was recovered and cut to provide a set of six 1-inch by 2-inch by 1/16-inch (25.4 mm by 50.8 mm by 1.5875 mm) flexural strength test pieces. The flexural strength test pieces were post-cured at 200° C. for two hours (7200 s) and then tested on an Instron machine with standard methods (ASTM D-790). The Instron machine was set at a 1 inch (25.4 mm) span, 0.02 inch per minute (0.0085 mm/s) crosshead speed and a 0.5 inch per minute (0.21166 mm/s) chart speed. The Barcol hardness value is on the 934-1 scale. The results are reported in Table I.

TABLE I

| | |
|---|---|
| Barcol Hardness | 74 |
| Flexural Strength, psi/kPa | 76,572/527,949 |
| Flexural Modulus, psi/kPa | 3,643,000/25,117,756 |

EXAMPLE 2

A. Preparation of Bismaleimide of Methylenedianiline

A 106.0 gram portion of maleic anhydride (1.08 moles) and 400 milliliters of N,N-dimethylformamide were added to a reactor and maintained under a nitrogen atmosphere with stirring. The stirred solution was cooled to 5° C. then 107.0 grams of methylenedianiline (0.54 mole) dissolved in 200 milliliters of N,N-dimethylformamide was added to the reactor over a sixty minute (3600 s) period and so as to maintain the reaction temperature at 5° to 10° C. After completion of the methylenedianiline in N,N-dimethylformamide solution addition the reactor was maintained at 5° to 10° C. for an additional 120 minutes (7200 s). The reactor was then allowed to warm to room temperature (25° C.), and the reaction product was removed and rotary evaporated at 55° to 60° C. under vacuum. After approximately 300 milliliters of N,N-dimethylformamide and water had distilled off, a voluminous light yellow colored precipitate formed and was recovered by filtration. The recovered precipitate was recrystallized from acetone and then dried in a vacuum oven at 80° C. The bismaleimide of methylenedianiline (172.6 grams) was recovered in 89.2 percent yield as a light yellow colored powder. Infrared spectrophotometric analysis of a potassium chloride pellet of the product confirmed the product structure. Nuclear magnetic resonance spectroscopy provided further confirmation of the product structure.

B. Preparation and B-Staging of a Bisphenol A Dicyanate, Bismaleimide of Methylene Dianiline and p-Isopropenylphenyl Cyanate Solution A 10.0 gram portion of the bismaleimide of methylenedianiline from A above and 220.0 grams of bisphenol A dicyanate prepared using the method of Example 1-B were combined to form a mixture. This mixture was heated to 150° C. and stirred for 10 minutes (600 s) to provide an amber colored solution. This solution was cooled to 75° C. then 20.0 grams of p-isopropenylphenyl cyanate from Example 1-A and 0.125 gram of cobalt naphthenate (6.0 percent active) were added. The resulting solution possessed a Brookfield viscosity of 50 cp at 75° C. B-staging (prepolymerization) of the solution was accomplished by heating at 120° C. for 2.5 hours (9000 s). The resulting B-staged product possessed a Brookfield viscosity of greater than 1000 cp (1 Pa's) at 120° C. and was recovered as a transparent, amber colored solid at room temperature (25° C.).

C. Use of a B-Staged Bisphenol A Dicyanate, Bismaleimide of Methylenedianiline and p-Isopropenylphenyl Cyanate Resin and Epoxide Resin Solution in Preparation of a Cured Glass Laminate A 50.0 gram portion of the B-staged bisphenol A dicyanate, bismaleimide of methylenedianiline and p-isopropenylphenyl cyanate resin from B abovr, 12.5 grams of a diglycidyl ether of bisphenol A having an epoxide equivalent weight (EEW) of 183 and 150 grams of methylene chloride were combined to form a solution. This solution was filtered and then 0.031 gram of cobalt naphthenate (6.0 percent active) was added. A set of three 12 inch by 12 inch (304.8 mm by 304.8 mm) woven fiberglass cloth pieces were then equally impregnated with the solution. The fiberglass cloth used was a commercial-grade product treated with a proprietary coupling agent (Burlington 76–28 electrical laminating cloth) and had an average weight of 0.14 gram per square inch (0.0217 g/cm$^2$). The set of impregnated cloths were allowed to dry for 1 hour (3600 s) at room temperature (25° C.) followed by additional drying in a vented forced air, convection-type oven for 20 minutes (1200 s) at 70° C. Each cloth was cooled and found to be tack-free at room temperature and then cut to provide ten 6 inch by 6 inch (152.4 mm by 152.4 mm) pieces which were loaded into a stainless steel frame and placed between stainless steel plates which had been treated with a silicone mold release. The plates were loaded into a 177° C. hot press (Pasadena Hydraulics, Inc., Model P-215)and maintained for two hours (7200 s) at 5000 psi (34.5 MPa). After this time a 6 inch by 6 inch by 1/16 inch (152.4 mm by 152.4 mm by 1.5785 mm) amber colored, rigid laminate was recovered and cut to provide a set of six 1 inch by 2 inch by 1/16 inch (25.4 mm by 50.8 mm by 1.5875 mm) flexural strength test pieces. The flexural strength test pieces were post-cured at 200° C. for two hours (7200 s) and then tested on an Instron machine with standard methods (ASTM D-790). The Instron machine was set at a 1 inch (25.4 mm) span, 0.02 inch per minute (0.00085 cm/s) crosshead speed and a 0.5 inch per minute (0.021166 cm/s) chart speed. The Barcol hardness value is on the 934-1 scale. The results are reported in Table II.

TABLE II

| Barcol Hardness | 75 |
|---|---|
| Flexural Strength, psi/kPa | 87,843/605,660 |
| Flexural Modulus, psi/kPa | 3,887,000/26,800,088 |

EXAMPLE 3

Portions (1.0 gram) of the resin solutions prepared in Example 1-D and Example 2-C for the impregnation of fiberglass cloths were devolatized to remove methylene chloride solvent then cured for two hours (7200 s) at 177° C. and post cured for two hours (7200 s) at 200° C. The cured resins were analyzed by differential scanning calorimetry (DSC) under a nitrogen atmosphere and at a scanning rate of 10° C. per minute (0.167° C./s) from 30° C. to 450° C. The glass transitions (Tg) are reported in Table III.

TABLE III

| Origin of Sample | Tg Midpoint (°C.) |
|---|---|
| Example 1-D | 183 |
| Example 2-C | 169 |

EXAMPLE 4

Portions of the cured resins from Example 3 were analyzed by thermogravimetric analysis (TGA). Weight loss was recorded as a function of temperature at a 10° C. per minute rate of increase and in a stream of nitrogen flowing at 35 cubic centimeters per minute. The results are reported in Table IV.

TABLE IV

| Origin of Cured Resin | Percent Weight Loss | | | | | |
|---|---|---|---|---|---|---|
| | 100° C. | 300° C. | 350° C. | 400° C. | 500° C. | 700° C. |
| Example 1-D | 0.1 | 1.2 | 3.8 | 21.0 | 81.9 | 85.4 |
| Example 2-C | 0 | 3.4 | 17.6 | 46.2 | 68.3 | 74.3 |

EXAMPLE 5

Preparation and Copolymerization of a Bisphenol A Dicyanate, p-Isopropenylphenyl Cyanate, Styrene and Epoxide Resin Solution A 6.875 gram portion of p-isopropenylphenyl cyanate prepared using the method of Example 1-A, 100.0 grams of bisphenol A dicyanate prepared using the method of Example 1-B, 124.93 grams of a diglycidyl ether of bisphenol A having an epoxide equivalent weight (EEW) of 183, 50.07 grams of styrene and 0.282 gram of cobalt naphthenate (6.0 percent active) were combined to form a solution maintained at 60° C. This solution was poured into a ⅛ inch (3.175 mm) mold made from a pair of glass plates and then placed in an oven and maintained at 130° C. for 2 hours (7200 s), 150° C. for 1 hour (3600 s), then 177° C. for 2 hours (7200 s). The transparent, light yellow colored, clear unfilled casting was demolded and used to prepare test pieces for tensile and flexural strength, flexural modulus, percent elongation and average Barcol hardness (934–1 scale) determinations. Mechanical properties of tensile (8) and flexural (8) test pieces were determined using an Instron machine with standard test methods (ASTM D-638 and D-790). The results are reported in Table V.

TABLE V

| Barcol Hardness | 43 |
|---|---|

TABLE V-continued

| | |
|---|---|
| Heat Distortion Temperature, °F./°C. | 274/134.4 |
| Tensile Strength, psi/kPa | 12,468/85,964 |
| Elongation % | 4.13 |
| Flexural Strength, psi/kPa | 23,673/163,221 |
| Flexural Modulus, psi/kPa | 563,000/3,881,772 |

COMPARATIVE EXPERIMENT A

Use of Bisphenol A Dicyanate in Preparatioon of a Cured Glass Laminate

A 55.0 gram portion of Bisphenol A dicyanate prepared using the method of Example 1-B, 150 grams of methylene chloride and 0.125 gram of cobalt naphthenate (6.0 percent active) were combined to form a solution. A set of three 12-inch by 12-inch (304.8 mm by 304.8 mm) woven fiberglass cloth pieces were then equally impregnated with the solution. The fiberglass cloth used was a commercial-grade product treated with a proprietary coupling agent (Burlington 76–28 electrical laminating cloth) and had an average weight of 0.14 gram per square inch (0.0217 g/cm$^2$). The set of impregnated cloths were allowed to dry for 1 hour (3600 s) at room temperature (25° C.) followed by additional drying and B-staging in a vented, forced-air, convection-type oven for 33 minutes (1980 s) at 100° C. then for 5 minutes (300 s) at 125° C. Each cloth was cooled and found to be tack-free at room temperature and then cut to provide ten 6-inch by 6-inch (152.4 mm by 152.4 mm) pieces which were loaded into a stainless steel frame and placed between stainless steel plates which had been treated with a silicone mold release. The plates were loaded into a 177° C. hot press (Pasadena Hydraulics, Inc., Model P-215) and maintained for two hours (7200 s) at 5000 psi (34.5 MPa). After this time a 6-inch by 6-inch by 1/16-inch (152.4 mm by 152.4 mm by 1.5785 mm) green colored, semi-transparent, rigid laminate was recovered and cut to provide a set of seven 1-inch by 2-inch by 1/16-inch (25.4 mm by 50.8 mm by 1.5875 mm) flexural strength test pieces. The flexural strength test pieces were post-cured at 200° C. for two hours (7200 s) and then tested using the method of Example 1-D. The results are reported in Table VI.

TABLE VI

| | |
|---|---|
| Barcol Hardness | 69 |
| Flexural Strength, psi/kPa | 86,097/593,622 |
| Flexural Modulus, psi/kPa | 4,075,000/28,096,310 |

EXAMPLE 6

Moisture Resistance of Cured Glass Laminates

Sets of 3 flexural strength test pieces from the cured fiberglass laminates of Example 1-D, Example 2-C and Comparative Experiment A, respectively, were weighed and then placed in individual glass jars, immersed under deionized water and then sealed. The jars were maintained for 8 days (192 hours) at 75° C. after which time the test pieces were removed, blotted, weighed and immediately tested on an Instron machine using the method of Example 1-D. The results are reported in Table VII with the unexposed values (zero exposure to water) provided for comparison.

TABLE VII

| | Example 1 | Example 2 | Comp. Expt. A |
|---|---|---|---|
| Barcol Hardness | | | |
| unexposed | 74 | 75 | 69 |
| exposed | 68 | 66 | 47 |
| (percent change) | (−8.11) | (−12.00) | (−31.88) |
| Flexural Strength | | | |
| unexposed, psi | 76,572 | 87,843 | 86,097 |
| kPa | 527,449 | 605,660 | 593,622 |
| exposed, psi | 59,189 | 64,302 | 39,724 |
| kPa | 408,096 | 443,349 | 273,889 |
| (percent change) | (−22.70) | (−26.80) | (−53.86) |
| Flexural Modulus | | | |
| unexposed, psi | 3,643,000 | 3,887,000 | 4,075,000 |
| kPa | 25,117,756 | 26,800,086 | 28,696,310 |
| exposed, psi | 3,643,000 | 3,804,000 | 2,461,500 |
| kPa | 25,117,756 | 26,227,819 | 16,971,550 |
| (percent change) | (0) | (−2.14) | (−39.61) |
| Weight (percent change) | +0.48 | +0.68 | +1.01 |

EXAMPLE 7

Infrared Spectrophotometric Analysis of Bisphenol A Dicyanate, p-Isopropenylphenyl Cyanate and Epoxide Resin Copolymer A sample of p-isopropenylphenyl cyanate of Example 1-A, the bisphenol A dicyanate of Example 1-B and the same diglycidyl ether of bisphenol A used in Example 1-C were analyzed by infrared spectrophotometric analysis as neat film samples on a sodium chloride plate. A sample of the cured resin of Example 3 (prepared by curing the bisphenol A dicyanate, p-isopropenylphenyl cyanate and epoxide resin solution of Example 1-D) was analyzed by infrared spectrophotometric analysis of a potassium bromide pellet. A portion (0.3 gram) of the bisphenol A dicyanate solution of Comparative Experiment A was devolatized to remove methylene chloride solvent then cured for two hours (7200 s) at 177° C. and post cured for two hours (7200 s) at 200° C. The cured resin was analyzed by infrared spectrophotometric analysis of a potassium bromide pellet. The results are reported in Table VIII.

The results demonstrate essentially complete conversion of cyanate groups, epoxide groups and alkenyl groups, present in the resin solution of Example 1-D used to prepare the copolymerized product in Example 3, to curing structures. A principle curing structure appears to be that observed at 1750 cm$^{-1}$ and proposed to be an oxazoline. The curing structure at 1700 cm$^{-1}$ is of unknown configuration but this absorbance may be from a carbonyl group generated from a ring opening reaction of a portion of the oxazoline groups during curing. Only a minor amount of a triazine group curing structure is formed based on comparison with the 1575 cm$^{-1}$ absorbance observed in the standard sample of cyclotrimerized bisphenol A dicyanate.

TABLE VIII

| Assignment of Absorbance | p-Isopropenylphenyl Cyanate[2] | Bisphenol A Dicyanate[2] | Diglycidyl Ether of Bisphenol A[2] | Copolymerized Product of Example 1-D |
|---|---|---|---|---|
| cyanate | 2220/2240 cm$^{-1}$ sharp, strong doublet | 2235/2265 cm$^{-1}$ sharp, strong doublet | none | none |
| oxazoline | none | none | none | 1750 cm$^{-1}$ sharp, strong |

TABLE VIII-continued

| Assignment of Absorbance | p-Isopropenylphenyl Cyanate[2] | Bisphenol A Dicyanate[2] | Diglycidyl Ether of Bisphenol A[2] | Copolymerized Product of Example 1-D |
|---|---|---|---|---|
| (unknown) | none | none | none | 1700 cm$^{-1}$ medium, shoulder |
| c=c stretch conjugated with benzene ring | 1630 cm$^{-1}$ sharp, shoulder | none | none | none |
| aromatic ring | 1600 cm$^{-1}$ | 1600 cm$^{-1}$ | 1610 cm$^{-1}$ | 1610 cm$^{-1}$ |
| triazine | none | none[1] | none | 1575 cm$^{-1}$ weak, shoulder |
| aromatic ring | 1520 cm$^{-1}$ | 1500 cm$^{-1}$ | 1510 cm$^{-1}$ | 1510 cm$^{-1}$ |
| epoxide | none | none | 910 cm$^{-1}$ | none |

[1]cyclotrimerization of bisphenol A dicyanate using cobalt naphthenate catalysis produced a distinct, strong 1575 cm$^{-1}$ band attributed to the triazine
[2]not an embodiment of the invention

I claim:
1. A composition which comprises
   (A) from about 1 to about 99 percent by weight of at least one alkenyl phenyl cyanate;
   (B) from about 1 to about 99 percent by weight of at least one material having an average of more than one vicinal epoxide group per molecule;
   (C) from zero to about 98 percent by weight of at least one aromatic polycyanate;
   (D) from zero to about 50 percent by weight of at least one polymaleimide; and
   (E) from about zero to about 98 percent by weight of at least one polymerizable ethylenically unsaturated aromatic material.
2. A composition of claim 1 wherein
   (i) component (A) is present in quantities of from about 1 to about 75 percent by weight;
   (ii) component (B) is present in quantities of from about 1 to about 75 percent by weight;
   (iii) component (C) is present in quantities of from about 5 to about 90 percent by weight;
   (iv) component (D) is present in quantities of from about zero to about 20 percent by weight; and
   (v) component (E) is present in quantities of from zero to about 50 percent by weight.
3. A composition of claim 2 wherein
   (i) component (A) is present in quantities of from about 5 to about 50 percent by weight;
   (ii) component (B) is present in quantities of from about 5 to about 50 percent by weight;
   (iii) component (C) is present in quantities of from about 25 to about 80 percent by weight;
   (iv) component (D) is present in quantities of from about zero to about 5 percent by weight; and
   (v) component (E) is present in quantities of from zero to about 20 percent by weight.
4. A composition of claim 1 wherein
   (i) component (A) is a material or mixture of materials represented by formula I in the specification;
   (ii) component (B) is a material or mixture of materials represented by formulas III and/or IV and/or V and/or VI in the specification;
   (iii) component (C) is a material or mixture of materials represented by formula VII and/or VIII and/or IX and/or X in the specification;
   (iv) component (D) is a mateial or mixture of materials represented by formulas XV and/or XVI and/or XVII in the specification; and
   (v) component (E) is a material or mixture of materials represented by formula XXII in the specification.
5. A composition of claim 4 wherein
   (i) component (A) is p-isopropenylphenyl cyanate, p-vinylphenyl cyanate, m-vinylphenyl cyanate, methyl-p-isopropenylphenyl cyanate, 3-chloro-4-isopropenylphenyl cyanate, p-allylphenyl cyanate, p-methallylphenyl cyanate, m-allylphenyl cyanate, 2,6-dimethyl-4-allylphenyl cyanate, or mixtures thereof;
   (ii) component (B) is a diglycidyl ether of resorcinol, a diglycidyl ether of bisphenol A, a diglycidyl ether of tetrabromobisphenol A, a triglycidyl ether of tris(hydroxyphenyl) methane, a polyglycidyl ether of a phenolformaldehyde novolac resin, a polyglycidyl ether of a dicyclopentadiene and phenol condensation product or mixtures thereof;
   (iii) component (C) is bisphenol A dicyanate, a dicyanate of dihydroxydiphenyl oxide, a dicyanate of resorcinol, a dicyanate of thiodiphenol, a dicyanate of sulfonyldiphenol, a dicyanate of tetrabromobisphenol A, a dicyanate of phenyl bisphenol A, a dicyanate of dihydroxybiphenyl, a dicyanate of tetrahydroxydiphenyl methane, a dicyanate of a dicyclopentadiene diphenol, a dicyanate of tetramethyltetrabromobisphenol A, a tricyanate of tris(hydroxyphenyl)methane, a dicyanate of dimethoxybisphenol A, a tetracyanate of tetrahydroxydiphenyl methane, a polycyanate of a dicyclopentadiene and phenol condensation product, a polycyanate of a phenolformaldehyde condensation product (novolac resin) or mixtures thereof;
   (iv) component (D) is N,N'-ethylenebismaleimide, N,N'-ethylenebis(2-methylmaleimide), N,N'-hexamethylenemaleimide, N,N'-(oxydi-p-phenylene)-bismaleimide, N,N'-(methylenedi-p-phenylene)bismaleimide, N,N'-(methylenedi-p-phenylene)bis(2-methylmaleimide), N,N'-(thiodi-p-phenylene)bismaleimide, N,N'-(sulfonyldi-m-phenylene)bismaleimide, N,N'-(isopropylidenedi-p-phenylene)-bismaleimide, a polymethylene polyphenylene polymaleimide or mixture thereof;
   (v) component (E) is styrene, a methylstyrene, a chlorostyrene, a bromostyrene, a t-butylstyrene, a methoxystyrene, a divinylbenzene, a propylstyrene, a chloromethylstyrene or mixture thereof.
6. A composition of claim 5 wherein said composition is a composition selected from
   (a) a mixture of bisphenol A dicyanate, p-isopropenyl cyanate and a diglycidyl ether of bisphenol A;
   (b) a mixture of bisphenol A dicyanate, bismaleimide of methylenedianiline and p-isopropenylphenyl cyanate;

(C) a mixture of p-isopropenylphenyl cyanate, a diglycidyl ether of bisphenol A, styrene and bisphenol A dicyanate; or (d) a mixture of p-isopropenylphenyl cyanate, a diglycidyl ether of bisphenol A, styrene, bisphenol A dicyanate and bismaleimide of methylenedianiline.

7. A product resulting from subjecting a composition of claim 1 to curing conditions in the presence or absence of a curing quantity of a suitable curing agent(s) or catalyst(s).

8. A product of claim 7 wherein said curing agent or catalyst is a cyclization catalyst.

9. A product of claim 8 wherein said cyclization catalyst is cobalt naphthenate, cobalt octoate or mixtures thereof.

10. A product resulting from subjecting a composition of claim 2 to curing conditions in the presence or absence of a curing quantity of a suitable curing agent(s) or catalyst(s).

11. A product of claim 10 wherein said curing agent or catalyst is a cyclization catalyst.

12. A product of claim 11 wherein said cyclization catalyst is cobalt naphthenate, cobalt octoate or mixtures thereof.

13. A product resulting from subjecting a composition of claim 3 to curing conditions in the presence or absence of a curing quantity of a suitable curing agent(s) or catalyst(s).

14. A product of claim 13 wherein said curing agent or catalyst is a cyclization catalyst.

15. A product of claim 14 wherein said cyclization catalyst is cobalt naphthenate, cobalt octoate or mixtures thereof.

16. A product resulting from subjecting a composition of claim 4 to curing conditions in the presence or absence of a curing quantity of a suitable curing agent(s) or catalyst(s).

17. A product of claim 16 wherein said curing agent or catalyst is a cyclization catalyst.

18. A product of claim 17 wherein said cyclization catalyst is cobalt naphthenate, cobalt octoate or mixtures thereof.

19. A product resulting from subjecting a composition of claim 5 to curing conditions in the presence or absence of a curing quantity of a suitable curing agent(s) or catalyst(s).

20. A product of claim 19 wherein said curing agent or catalyst is a cyclization catalyst.

21. A product of claim 20 wherein said cyclization catalyst is cobalt naphthenate, cobalt octoate or mixtures thereof.

22. A product resulting from subjecting a composition of claim 6 to curing conditions in the presence or absence of a curing quantity of a suitable curing agent(s) or catalyst(s).

23. A product of claim 22 wherein said curing agent or catalyst is a cyclization catalyst.

24. A product of claim 23 wherein said cyclization catalyst is cobalt naphthenate, cobalt octoate or mixtures thereof.

25. A product of claim 7 which results in an electrical or structural laminate or composite.

26. A product of claim 8 which results in an electrical or structural laminate or composite.

27. A product of claim 9 which results in an electrical or structural laminate or composite.

28. A product of claim 10 which results in an electrical or structural laminate or composite.

29. A product of claim 11 which results in an electrical or structural laminate or composite.

30. A product of claim 12 which results in an electrical or structural laminate or composite.

31. A product of claim 13 which results in an electrical or structural laminate or composite.

32. A product of claim 14 which results in an electrical or structural laminate or composite.

33. A product of claim 15 which results in an electrical or structural laminate or composite.

34. A product of claim 16 which results in an electricl or structural laminate or composite.

35. A product of claim 17 which results in an electrical or structural laminate or composite.

36. A product of claim 18 which results in an electrical or structural laminate or composite.

37. A product of claim 19 which results in an electrical or structural laminate or composite.

38. A product of claim 20 which results in an electrical or structural laminate or composite.

39. A product of claim 21 which results in an electrical or structural laminate or composite.

40. A product of claim 22 which results in an electrical or structural laminate or composite.

41. A product of claim 23 which results in an electrical or structural laminate or composite.

42. A product of claim 24 which results in an electrical or structural laminate or composite.

* * * * *